US011759375B2

(12) United States Patent
Hasse et al.

(10) Patent No.: US 11,759,375 B2
(45) Date of Patent: *Sep. 19, 2023

(54) DISPOSABLE ABSORBENT ARTICLES

(71) Applicant: The Procter & Gamble Company, Cincinnati, OH (US)

(72) Inventors: Margaret Henderson Hasse, Wyoming, OH (US); Luke Robinson Magee, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 353 days.

This patent is subject to a terminal disclaimer.

(21) Appl. No.: 17/004,054

(22) Filed: Aug. 27, 2020

(65) Prior Publication Data

US 2020/0390614 A1 Dec. 17, 2020

Related U.S. Application Data

(63) Continuation of application No. 15/785,864, filed on Oct. 17, 2017, now Pat. No. 10,799,402, which is a continuation of application No. 14/206,001, filed on Mar. 12, 2014, now Pat. No. 9,820,894.

(60) Provisional application No. 61/804,271, filed on Mar. 22, 2013.

(51) Int. Cl.
*A61F 13/15* (2006.01)
*A61F 13/49* (2006.01)
*A61F 13/496* (2006.01)

(52) U.S. Cl.
CPC ...... *A61F 13/49017* (2013.01); *A61F 13/496* (2013.01); *A61F 13/4906* (2013.01); *A61F 13/49011* (2013.01); *A61F 13/49012* (2013.01); *A61F 13/49014* (2013.01); (Continued)

(58) Field of Classification Search
CPC .. A61F 2013/49092; A61F 2013/49025; A61F 13/59014; A61F 13/59012; A61F 13/496; A61F 13/4906; A61F 13/49011; A61F 13/49017

See application file for complete search history.

(56) References Cited

U.S. PATENT DOCUMENTS

| 4,340,706 A | 7/1982 | Obayashi et al. |
| 4,507,438 A | 3/1985 | Obayashi et al. |
| 4,666,983 A | 5/1987 | Tsubankimoto et al. |

(Continued)

FOREIGN PATENT DOCUMENTS

| CN | 1713875 A | 12/2005 |
| DE | 10204937 A1 | 8/2003 |

(Continued)

OTHER PUBLICATIONS

P&G 12819, All Office Actions for U.S. Patent App. U.S. Appl. No. 14/206,001.

(Continued)

*Primary Examiner* — Jacqueline F Stephens
(74) *Attorney, Agent, or Firm* — Charles R. Matson

(57) ABSTRACT

An absorbent article comprising a first and second plurality of elastics. The first plurality of elastics may be disposed in a front and a crotch region. The second plurality of elastics may be disposed in a back region and the crotch region. The first and second plurality of elastics may be linear and parallel with a transverse axis of the article.

20 Claims, 13 Drawing Sheets

(52) U.S. Cl.
CPC .............. *A61F 13/49015* (2013.01); *A61F 2013/49025* (2013.01); *A61F 2013/49092* (2013.01)

(56) References Cited

U.S. PATENT DOCUMENTS

| | | | |
|---|---|---|---|
| 5,266,392 A | 11/1993 | Land | |
| 5,281,683 A | 1/1994 | Yano et al. | |
| 5,331,059 A | 7/1994 | Engelhardt et al. | |
| 5,340,648 A | 8/1994 | Rollins | |
| 5,409,711 A | 4/1995 | Dahmen et al. | |
| 5,501,756 A | 3/1996 | Rollins | |
| 5,507,909 A | 4/1996 | Rollins | |
| 5,532,323 A | 7/1996 | Yano et al. | |
| 5,574,121 A | 11/1996 | Irie et al. | |
| 5,837,789 A | 11/1998 | Stockhausen et al. | |
| 5,849,816 A | 12/1998 | Suskind et al. | |
| 6,077,375 A | 6/2000 | Kwok | |
| 6,143,821 A | 11/2000 | Houben | |
| 6,200,635 B1 | 3/2001 | Kwok | |
| 6,235,137 B1 | 5/2001 | Van Eperen | |
| 6,265,488 B1 | 7/2001 | Fujino et al. | |
| 6,361,634 B1 | 3/2002 | White | |
| 6,472,478 B1 | 10/2002 | Funk et al. | |
| 6,503,979 B1 | 1/2003 | Funk et al. | |
| 6,520,237 B1 | 2/2003 | Bolyard | |
| 6,559,239 B1 | 5/2003 | Riegel et al. | |
| 6,582,518 B2 | 6/2003 | Riney | |
| 6,610,161 B2 | 8/2003 | Erdman | |
| 6,613,146 B2 | 9/2003 | Bolyard | |
| 6,632,385 B2 | 10/2003 | Kauschke | |
| 6,645,569 B2 | 11/2003 | Cramer | |
| 6,652,693 B2 | 11/2003 | Buriss | |
| 6,657,015 B1 | 12/2003 | Riegel et al. | |
| 6,719,846 B2 | 4/2004 | Nakamura | |
| 6,737,102 B1 | 5/2004 | Saidman | |
| 6,803,103 B2 | 10/2004 | Kauschke | |
| 6,809,158 B2 | 10/2004 | Ikeuchi et al. | |
| 6,863,933 B2 | 3/2005 | Cramer | |
| 7,112,621 B2 | 9/2006 | Rohrbaugh | |
| 7,199,211 B2 | 4/2007 | Popp et al. | |
| 7,250,481 B2 | 7/2007 | Jaworek et al. | |
| 7,652,111 B2 | 1/2010 | Hermeling et al. | |
| 7,687,596 B2 | 3/2010 | Hermeling et al. | |
| 7,744,576 B2 | 6/2010 | Busam et al. | |
| 7,772,420 B2 | 8/2010 | Hermeling et al. | |
| 7,838,722 B2 | 11/2010 | Blessing et al. | |
| 8,124,229 B2 | 2/2012 | Stueven et al. | |
| 8,180,603 B2 | 5/2012 | Blessing et al. | |
| 8,186,296 B2 | 5/2012 | Brown | |
| 8,236,715 B2 | 8/2012 | Schmidt et al. | |
| 8,308,706 B2 | 11/2012 | Fukae | |
| 8,389,658 B2 | 3/2013 | Stueven et al. | |
| 8,581,019 B2 | 11/2013 | Carlucci et al. | |
| 8,728,051 B2 | 5/2014 | Lu et al. | |
| 8,748,000 B2 | 6/2014 | Stueven et al. | |
| 8,939,957 B2 | 1/2015 | Raycheck | |
| 8,979,815 B2 | 3/2015 | Roe et al. | |
| 9,023,006 B2 | 5/2015 | Takino et al. | |
| 9,060,904 B2 | 6/2015 | Hundorf et al. | |
| 9,072,634 B2 | 7/2015 | Hundorf et al. | |
| 9,375,358 B2 | 6/2016 | Ehrnsperger et al. | |
| 10,799,402 B2 * | 10/2020 | Hasse | A61F 13/49017 |
| 2002/0045877 A1 | 4/2002 | Shimada et al. | |
| 2002/0197695 A1 | 12/2002 | Gluckmann et al. | |
| 2003/0148684 A1 | 8/2003 | Cramer | |
| 2004/0243083 A1 | 12/2004 | Matsuda et al. | |
| 2005/0008839 A1 | 1/2005 | Cramer | |
| 2005/0165208 A1 | 7/2005 | Popp et al. | |
| 2006/0057921 A1 | 3/2006 | Turi et al. | |
| 2006/0173435 A1 | 8/2006 | Nakajima et al. | |
| 2006/0244166 A1 | 11/2006 | Wada et al. | |
| 2007/0073262 A1 | 3/2007 | Babusik et al. | |
| 2007/0093767 A1 | 4/2007 | Carlucci et al. | |
| 2008/0051755 A1 | 2/2008 | Otsubo | |
| 2008/0287898 A1 | 11/2008 | Guzman et al. | |
| 2008/0312619 A1 | 12/2008 | Ashton et al. | |
| 2008/0312620 A1 | 12/2008 | Ashton et al. | |
| 2008/0312621 A1 | 12/2008 | Hundorf et al. | |
| 2008/0312622 A1 | 12/2008 | Hundorf et al. | |
| 2008/0312628 A1 | 12/2008 | Hundorf et al. | |
| 2009/0318884 A1 | 12/2009 | Meyer et al. | |
| 2010/0040826 A1 | 2/2010 | Autran | |
| 2010/0191212 A1 | 7/2010 | Torigoshi et al. | |
| 2010/0193111 A1 | 8/2010 | Wada et al. | |
| 2011/0077609 A1 | 3/2011 | Kuwano et al. | |
| 2011/0106039 A1 | 5/2011 | Saito et al. | |
| 2012/0078212 A1 | 3/2012 | Kobayashi et al. | |
| 2012/0302985 A1 | 11/2012 | Mukai et al. | |
| 2012/0316526 A1 | 12/2012 | Rosati et al. | |
| 2012/0316528 A1 | 12/2012 | Kreuzer et al. | |
| 2013/0213355 A1 | 8/2013 | Nishikawa et al. | |
| 2013/0310795 A1 | 11/2013 | Glahn et al. | |
| 2013/0331807 A1 | 12/2013 | Ichihara et al. | |
| 2014/0163503 A1 | 6/2014 | Arizti et al. | |
| 2014/0163511 A1 | 6/2014 | Roe et al. | |
| 2014/0288523 A1 | 9/2014 | Hasse | |
| 2014/0371701 A1 | 12/2014 | Bianchi et al. | |
| 2016/0270971 A1 | 9/2016 | Raycheck et al. | |
| 2016/0270973 A1 | 9/2016 | Raycheck et al. | |
| 2016/0270975 A1 | 9/2016 | Prakash et al. | |
| 2016/0270978 A1 | 9/2016 | Prakash et al. | |
| 2016/0270979 A1 | 9/2016 | Prakash et al. | |
| 2016/0270980 A1 | 9/2016 | Raycheck et al. | |
| 2016/0270981 A1 | 9/2016 | Raycheck et al. | |
| 2016/0270983 A1 | 9/2016 | Roe et al. | |
| 2016/0270985 A1 | 9/2016 | Raycheck et al. | |
| 2018/0036181 A1 | 2/2018 | Hasse et al. | |

FOREIGN PATENT DOCUMENTS

| | | |
|---|---|---|
| JP | 2009178382 | 1/2009 |
| JP | 2009082482 A | 4/2009 |
| JP | 2010051667 | 3/2010 |
| RU | 2197213 C2 | 1/2003 |
| WO | WO 1990015830 A1 | 12/1990 |
| WO | WO 1993021237 A1 | 10/1993 |
| WO | 2004078082 A1 | 9/2004 |
| WO | 2004105664 A1 | 12/2004 |
| WO | 2005007051 A1 | 1/2005 |
| WO | WO 2007144838 A1 | 12/2007 |
| WO | WO 2009155265 A2 | 12/2009 |
| WO | WO 2000002511 A1 | 1/2010 |
| WO | 2012063460 A1 | 5/2012 |

OTHER PUBLICATIONS

P&G 12819C, All Office Actions for U.S. Patent App. U.S. Appl. No. 15/785,864.
PCT International Search Report and Written Opinion, PCT/US2014/031385, dated Jul. 2, 2014.
Third Party Opposition filed for European Patent Application Ser. No. 14723595.6, Dated Apr. 22, 2021; 19 pages.

* cited by examiner

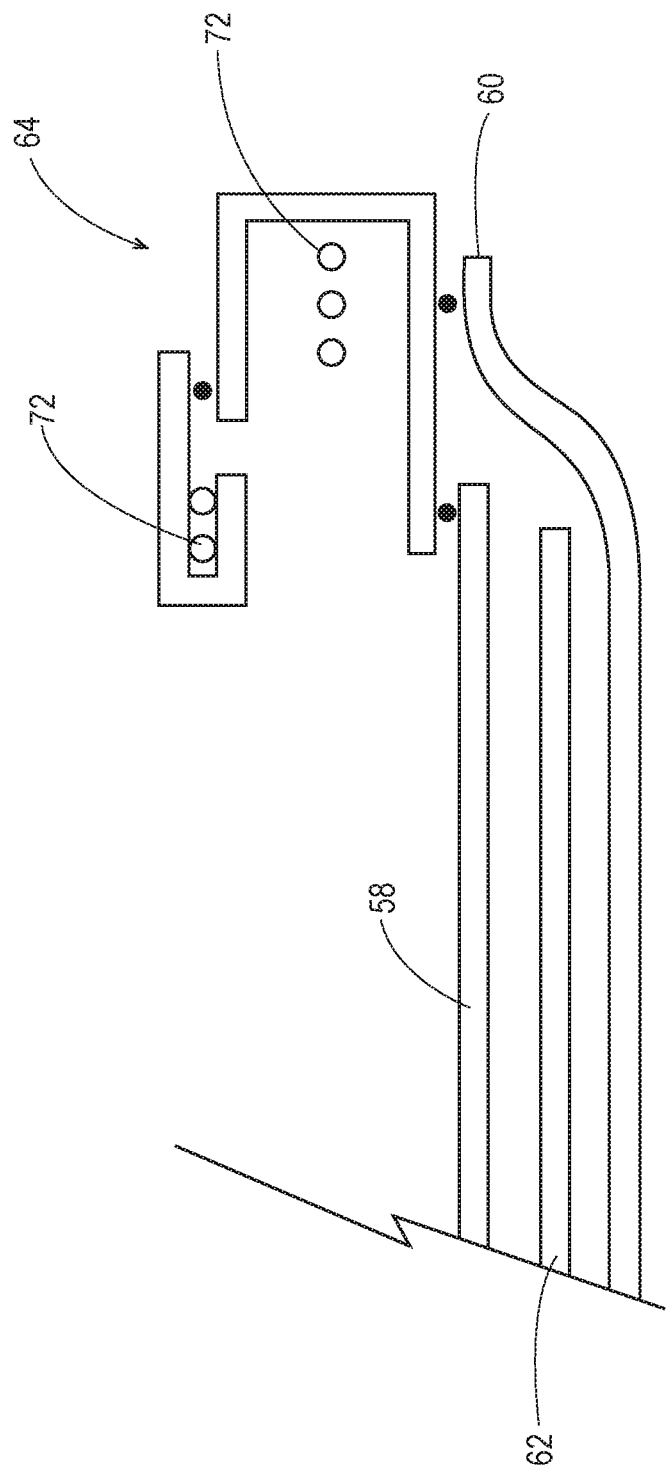

DISPOSABLE ABSORBENT ARTICLES

CROSS REFERENCE TO RELATED APPLICATIONS

This application is a continuation of U.S. patent application Ser. No. 15/785,864, filed on Oct. 17, 2017, which is a continuation of U.S. patent application Ser. No. 14/206,001, filed on Mar. 12, 2014, which claims the benefit of U.S. Provisional Patent Application Ser. No. 61/804,271, filed on Mar. 22, 2013, the entire disclosures of which are hereby incorporated by reference.

FIELD OF THE INVENTION

The present invention relates to disposable absorbent articles comprising linear elastics in the crotch region.

BACKGROUND OF THE INVENTION

Many adult incontinence products comprise elastic strands as the stretch engine in the waist region, where the strands are laminated between a single outer cover nonwoven and two discrete inner nonwoven belts. While most of the strands are parallel and run in the lateral direction in the waist regions of these products. Curved elastics often follow the leg cutout in the crotch region and the waist regions adjacent to the crotch region. Curving the elastics, however can be complicated and can slow the production of these products. Applicants disclose a design below that provides a full outer cover nonwoven without the need to include curved elastics. In fact, Applicants provide for straight elastics that extend into the crotch from both the front and rear waist regions, thus providing for articles that are simpler to make and that provide for increased coverage (especially in the rear) and that fit a broad range of consumers.

Applicants have also disclosed the combination of leg cutouts that provide for improved fit and coverage in combination with Applicants' disclosed elastic profile. And, further, Applicants have disclosed embodiments that may add leg cuffs to the center chassis to further improve protection against leaks.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 5B is a schematic cross section view taken along line 5-5 in FIG. 3 of an alternative embodiment example of a folded leg cuff suitable in one embodiment of the invention;

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and to be recycled, composted or otherwise disposed of in an environmentally compatible manner). The pull-on garment may be "absorbent" such that it absorbs and contains the various exudates discharged from the body.

As used herein, the term "absorbent article" refers to pull-on garments generally worn by infants and other incontinent individuals to absorb and contain urine, feces and/or menses. It should be understood, however, that the term absorbent article is also applicable to other garments such as training pants, incontinent briefs, feminine hygiene garments or panties, and the like.

As used herein, the terms "elastic," "elastomer," and "elastomeric" refer to a material which generally is able to extend to a strain of at least 50% without breaking or rupturing, and is able to recover substantially to its original dimensions, accounting for set, after the deforming force has been removed.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

Figure 1:
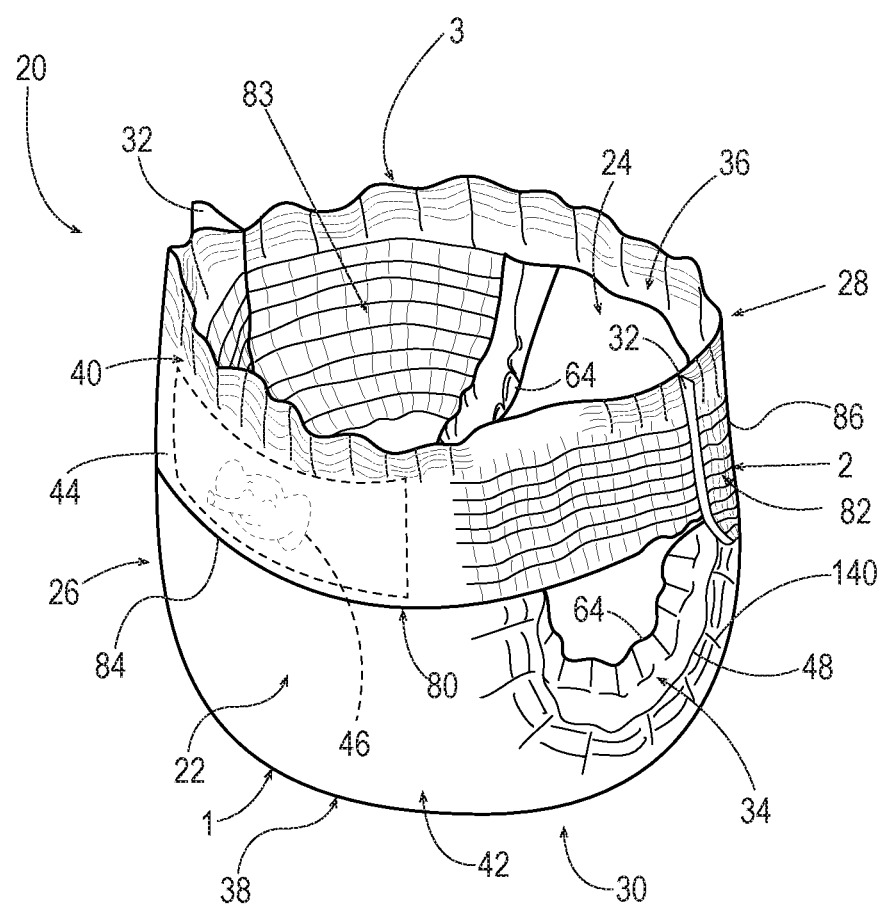
FIG. 1 is a perspective view of an exemplary disposable pull-on garment in a typical in-use configuration.
Figure 2:
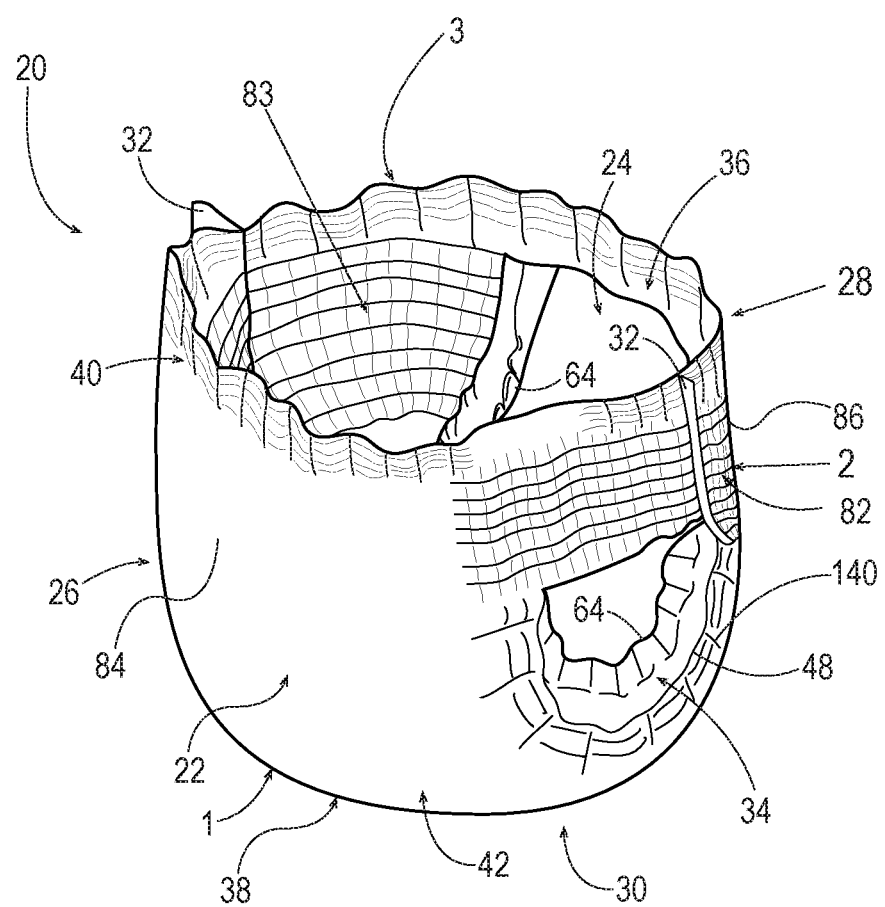
FIG. 2 is a perspective view of an exemplary disposable pull-on garment in a typical in-use configuration.

FIG. 1 is a perspective view of the absorbent article 20. FIG. 2 is a perspective view of the absorbent article 20. The absorbent article 20 has a longitudinal centerline L1 and a transverse centerline T1 (refer to FIG. 3 as well). The absorbent article 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. Also referring to FIGS. 1-3, the absorbent article 20 comprises a main portion 1, a side portion 2, and a waist portion 3.

Figure 3:
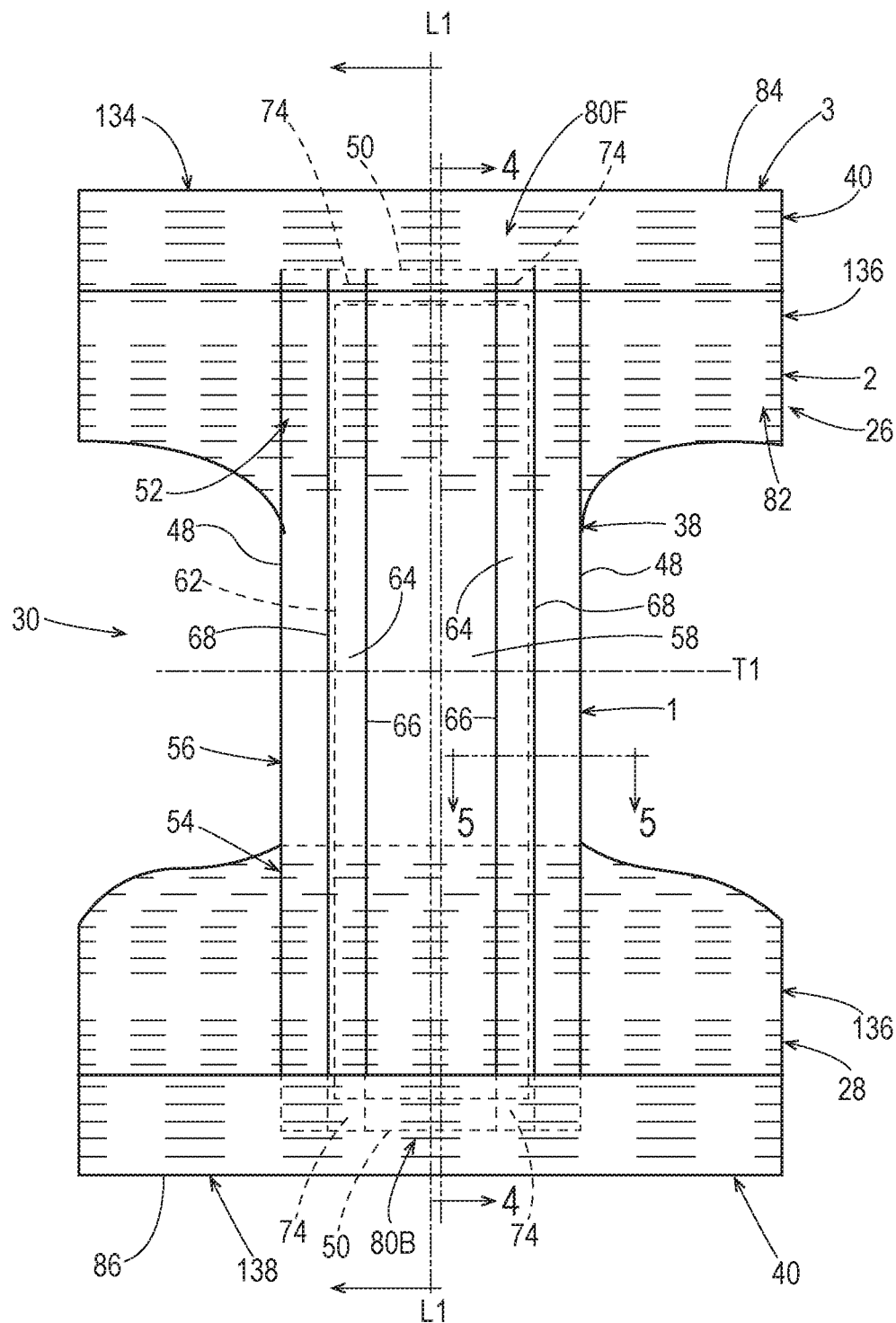
FIG. 3 is a plan view of the pull-on garment in its flat uncontracted condition showing the inner surface.
Figure 6:
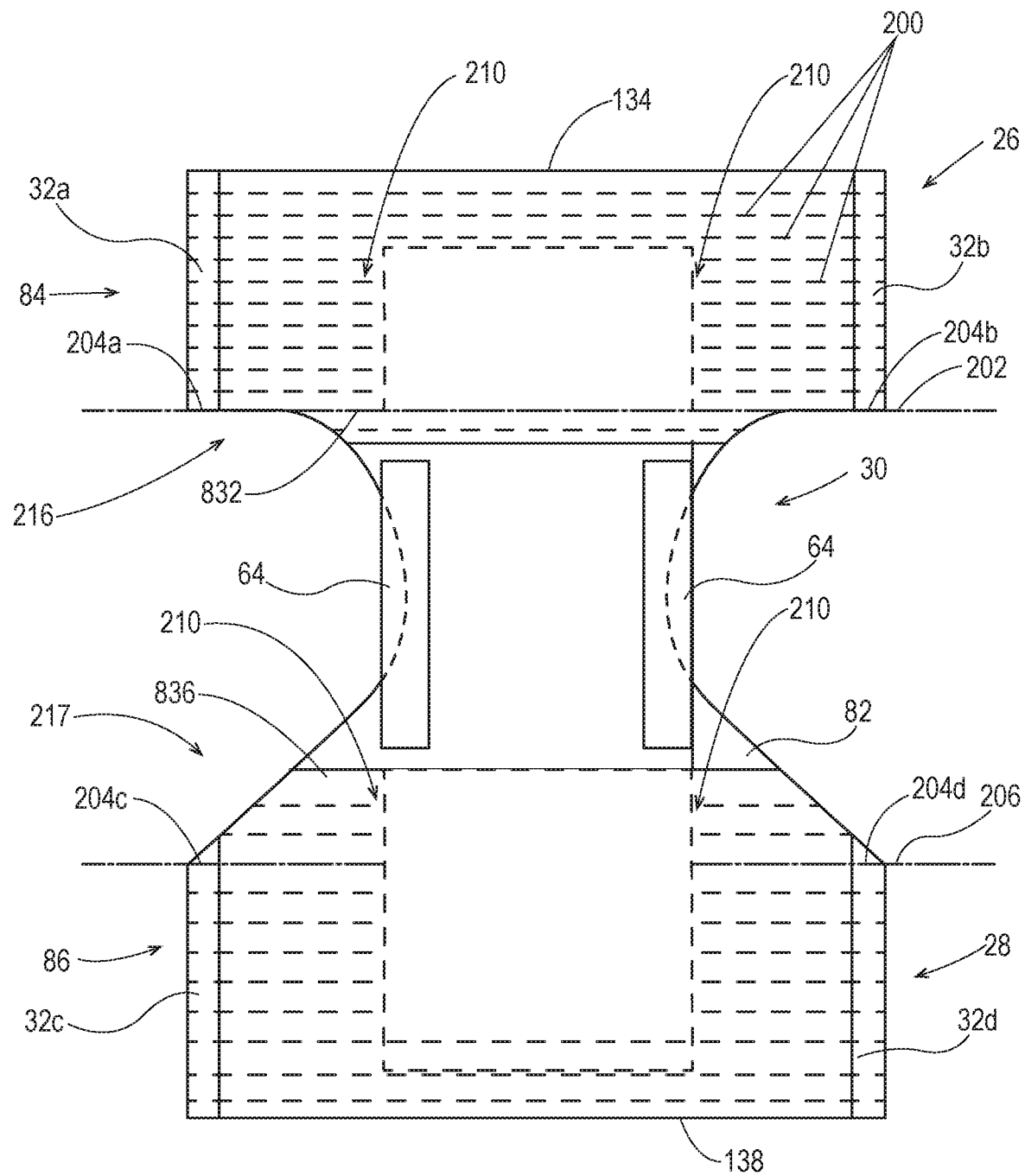
FIG. 6 is a plan view of the pull-on garment of FIG. 4D in its flat uncontracted condition showing the inner surface.

In the embodiment shown in FIGS. 1 and 3, the absorbent article 20 comprises an absorbent main body 38 (hereinafter may be referred to as "main body" or "central chassis") to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 jointly define the leg opening 34. As shown in FIG. 3 and FIG. 6, the portions of the belts making up leg openings 34 may be shaped. In the FIG. 3 embodiment, the front belt 84 may be concave and the rear belt may have a convex portion. Alternatively, both the front and rear belts may be concave or both may be convex. Also alternatively, the front belt may be convex and the rear belt may be concave. While FIG. 3 illustrates discrete first belt layers 83, FIG. 6 illustrates a full outer cover nonwoven first belt layer 82. In FIG. 6, the leg cutout also cuts through the second belt layers 83a and b.

In the embodiment shown in FIG. 2 the absorbent article 20 comprises an absorbent main body 38 to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 jointly define the leg opening 34. One or more of the belt layers may extend from a first waist edge 134 in a first waist region 26 through the crotch region to a longitudinally opposing second waist edge 138 in a second waist region 28 and may form a portion or the whole of the outer surface of the absorbent article 20.

The absorbent main body 38 absorbs and contains body exudates disposed on the main body 38. In the embodiment shown in FIG. 3, the main body 38 has a generally rectangular shape having a longitudinal centerline L1, a transverse centerline T1, left and right longitudinally extending side edges 48 (hereinafter may be referred to as "longitudinal side edge") and front and back transversely extending end edges 50 (hereinafter may be referred to as "transverse end edge"). The main body 38 also has waist panels (i.e., a front waist panel 52 positioned in the front waist region 26 of the absorbent article 20 and a back waist panel 54 positioned in the back waist region 28) and a crotch panel 56 in the crotch region 30 between the front and back waist panels 52, 54.

Figure 4A:
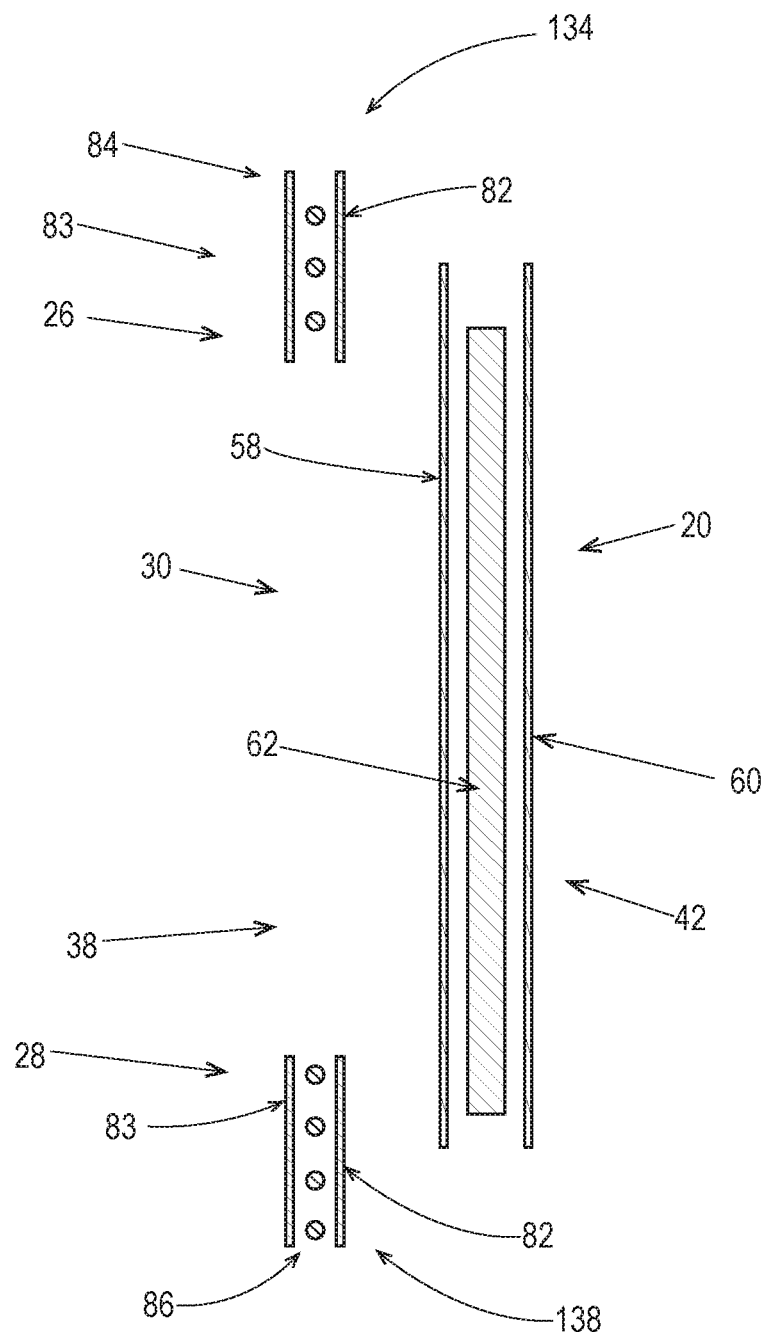
FIG. 4A is a schematic cross section view of a first embodiment taken along line 4-4 in FIG. 3 of an exemplary disposable pull-on garment.
Figure 4B:
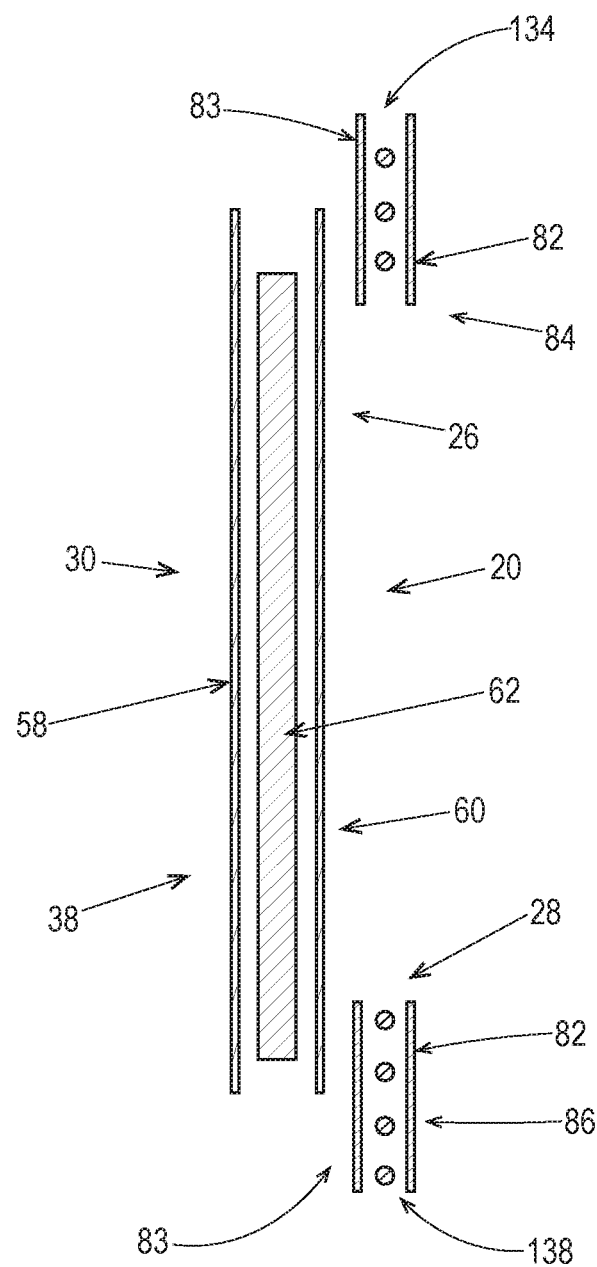
FIG. 4B is a schematic cross section view of a second embodiment taken along line 4-4 in FIG. 3 of an exemplary disposable pull-on garment.

In the embodiment shown in FIGS. 4A and 4B, the absorbent articles 20 may comprise front and rear belts 84, 86 intended to encircle at least a portion of the waist of the wearer, the front and rear belt portions 84, 86 being connected by a main body 38 forming the crotch region 30 of the absorbent article 20. The front and rear belts 84 and 86 may be formed from a first belt layer forming a portion of the outer surface 22 of the absorbent article, the first belt layer 82 may be formed of two longitudinally spaced webs of material. The front and rear belts 84 and 86 may also comprise a second belt layer 83 forming a portion of the inner surface 24 of the absorbent article 20, the second belt layer 83 may also be formed of two longitudinally spaced webs of material. The second belt layer may also be discontinuous and spaced apart in a transverse direction. The first and second belt layers 82, 83 may be formed of substantially the same material or may comprise different materials. The first and second belt layers 82, 83 may be formed from nonwovens, films, foams, elastic nonwoven, or combinations thereof. The front and rear belts 84, 86 may also comprise an elastomeric material disposed between the first and second belt layers 82, 83. The elastomeric material may comprise one or more elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer. The main body 38 (also referred to as a central chassis) of the absorbent article may comprise an outer surface 22, backsheet 60, an inner surface 24, topsheet 58, and an absorbent core 62 disposed between the topsheet 58 and the backsheet 60. The backsheet may be formed of a nonwoven material, woven material, films or laminates comprising a combination of one or more of these materials. In one embodiment the backsheet is a film and nonwoven laminate wherein the nonwoven of the laminate is the outer cover layer. In addition, the main body 38 may comprise elasticized barrier leg cuffs 64 disposed at or adjacent the side edges of the main body. The front and rear belts 84, 86 may overlap at least a portion of the main body and one or both of the belt portions may be disposed on the outer surface of the main body or alternatively on the inner surface of the main body. A portion of the second belt layer and/or a portion of the first belt layer may be directly attached to the outer cover layer. Alternatively, the front belt and rear belt 84, 86 may comprise longitudinally spaced webs of material forming a first surface of the belt wherein the webs are folded along the waist edge, or alternatively the leg opening edge, of the belt to wrap the elastomeric material and form at least a portion of the second surface of the belt. In other words, at least a portion of the inner surface and outer surface of each of the belt portions may be formed from a single web of material.

Figure 4C:
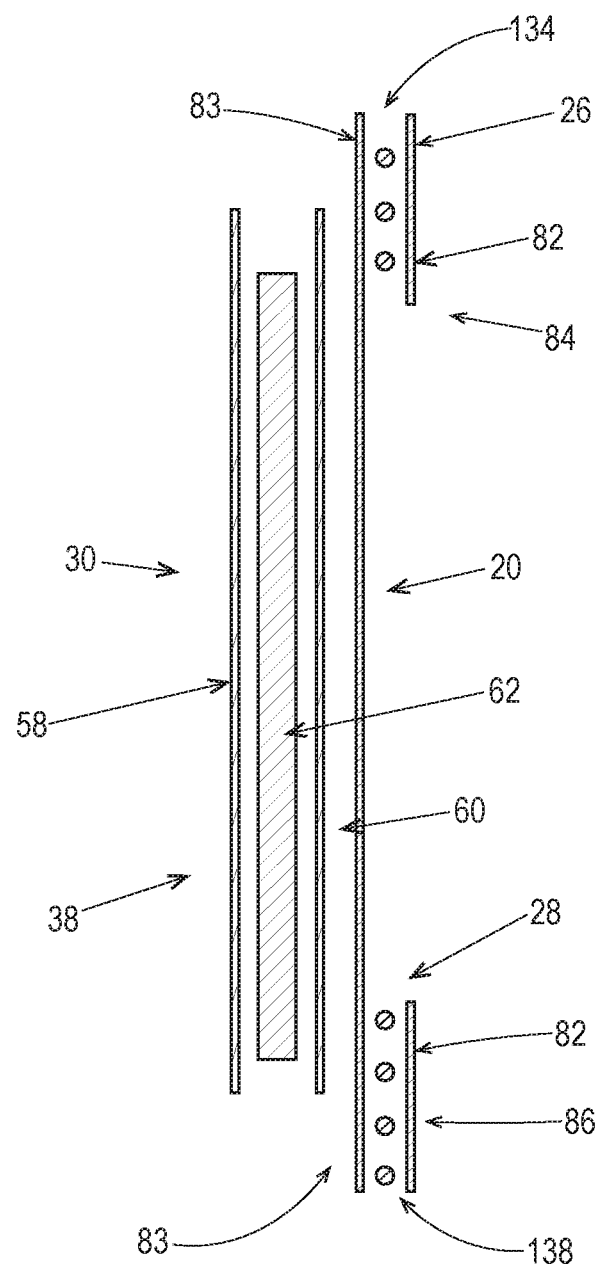
FIG. 4C is a schematic cross section view of a third embodiment taken along line 4-4 in FIG. 3 of an exemplary disposable pull-on garment.
Figure 4D:
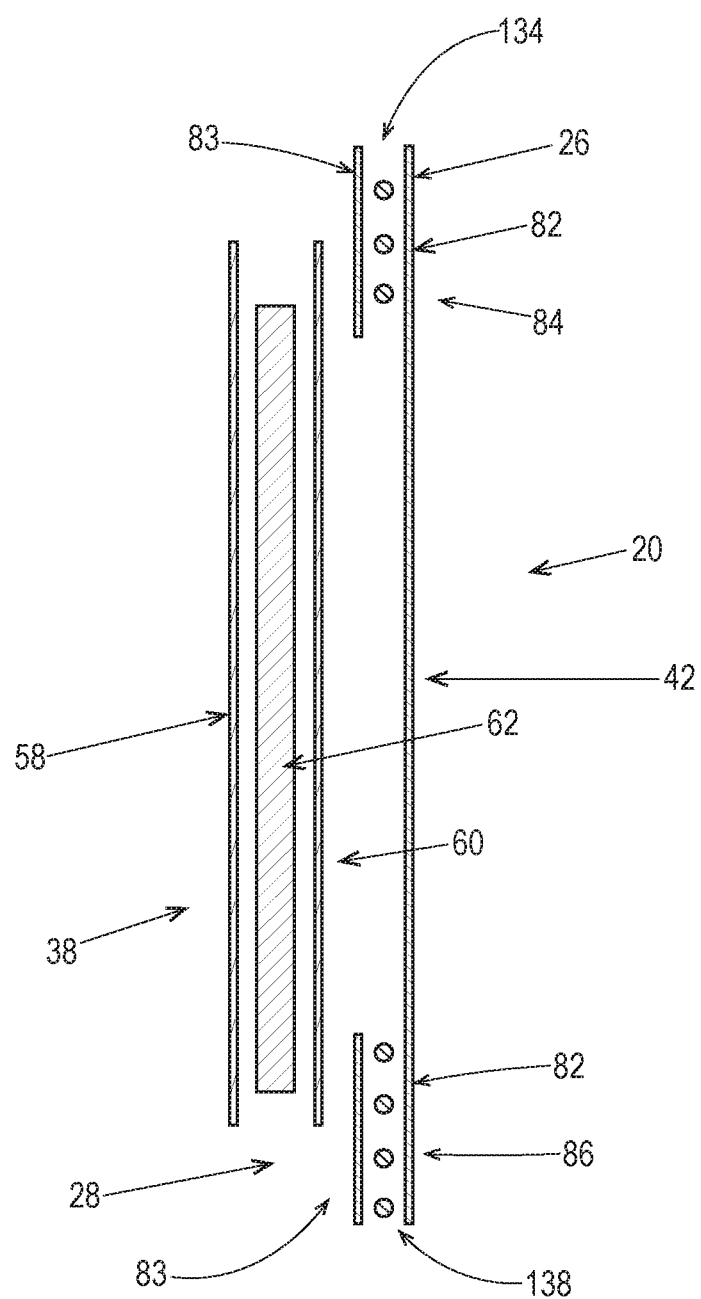
FIG. 4D is a schematic cross section view of a fourth embodiment taken along line 4-4 in FIG. 3 of an exemplary disposable pull-on garment.

In the embodiment shown in FIGS. 4C and 4D, the absorbent articles 20 may comprise front and rear extensible belts 84, 86 disposed in the front and rear waist regions 26, 28 respectively and intended to encircle at least a portion of the waist of the wearer, the front and rear belts 84, 86 being connected by the main body that forms the crotch region 30 of the article. The first and second belt may be formed from a first belt layer 82 (e.g., a "full outer cover nonwoven" or an "outer cover web") extending from a first waist edge 134 in a first waist region 26 through the crotch region to a longitudinally opposing second waist edge 138 in a second waist region 28 and forming a portion of the outer surface of the absorbent article 20. The front and rear belts 84, 86 also may comprise a second belt layer 83a and b (e.g., an "inner belt web") forming a portion of the inner surface 24 of the absorbent article, the second belt layer may be formed of two longitudinally spaced webs of material. The first and second belt portions may also comprise an elastomeric material 200 (e.g., "elastic elements" or "elastics") disposed between the first and second belt layers. The elastomeric material may comprise elastic strands, elastomeric films, elastomeric ribbons, elastomeric nonwovens, elastomeric filaments, elastomeric adhesives, elastomeric foams, scrims or combinations thereof. The main body 38 ("central or center chassis") of the absorbent article may comprise an outer surface 22, backsheet 60, an inner surface 24, topsheet 58, and an absorbent core 62 disposed between the topsheet 58 and the backsheet 60. The first belt layer may form a portion of the outer surface 22. In addition, the main body may comprise elasticized barrier leg cuffs 64 disposed at or adjacent the side edges of the main body. The second belt layer may overlap at least a portion of the main body and one or both of the second belt layer webs may form the outer surface of the first belt layer or alternatively the inner surface of the first belt layer. Alternatively, the front portion and/or the rear portion of the first belt layer 82 may be folded along the waist edge of the belt region to wrap the elastomeric material and form a portion of the second belt layer of one or both of the front and rear belt portions 84, 86. In other words, the inner surface and outer surface of each of the belt portions may be formed from a single web of material. FIG. 6 is plan view of the embodiment consistent with FIG. 4D.

As can be seen in FIG. 6, the elastics 200 in the front and/or rear regions 26, 28 may extend into the crotch region 30 (that is, the first plurality of elastics 216 and the second plurality of elastics 217 may be disposed in the front and/or rear regions 26, 28, as well as the crotch region). The front and crotch regions 26, 30 may be separated by a first axis 202 struck between a leg end edge 204a of the first side seam 32a to a leg end edge 204a of the second side seam 32b, along the first belt layer 82, the first axis 202 defining the transition between the front region 26 and the crotch region 30. Further, the rear and crotch regions 28, 30 may be separated by a second axis 206 struck between a leg end edge 204c of the first side seam 32a to a leg end edge 204d of the second side seam 32b, along the second belt layer 83, the second axis 206 defining the transition between the rear region 28 and the crotch region 30. It should be understood that the seams are opened and the article is laid flat such that 32a-d indicate where the seam is formed when the front and back belts are joined together.

FIG. 6 also illustrates that a majority of the elastics 200 may not overlap the center chassis 38. It may be desirable that none of the elastics 200 overlap the center chassis 38. In the embodiment illustrated in FIG. 6, only one or two overlap the end edges of the center chassis 38. It may also be desirable to overlap a portion of the center chassis 38, excluding the absorbent core 62.

One way to keep elastics from overlapping the absorbent core is to sever an unglued area of the elastics prior to placing the absorbent core onto the belts. The elastics can then snap back to a section of glued elastics (e.g., 210).

Figure 4E:
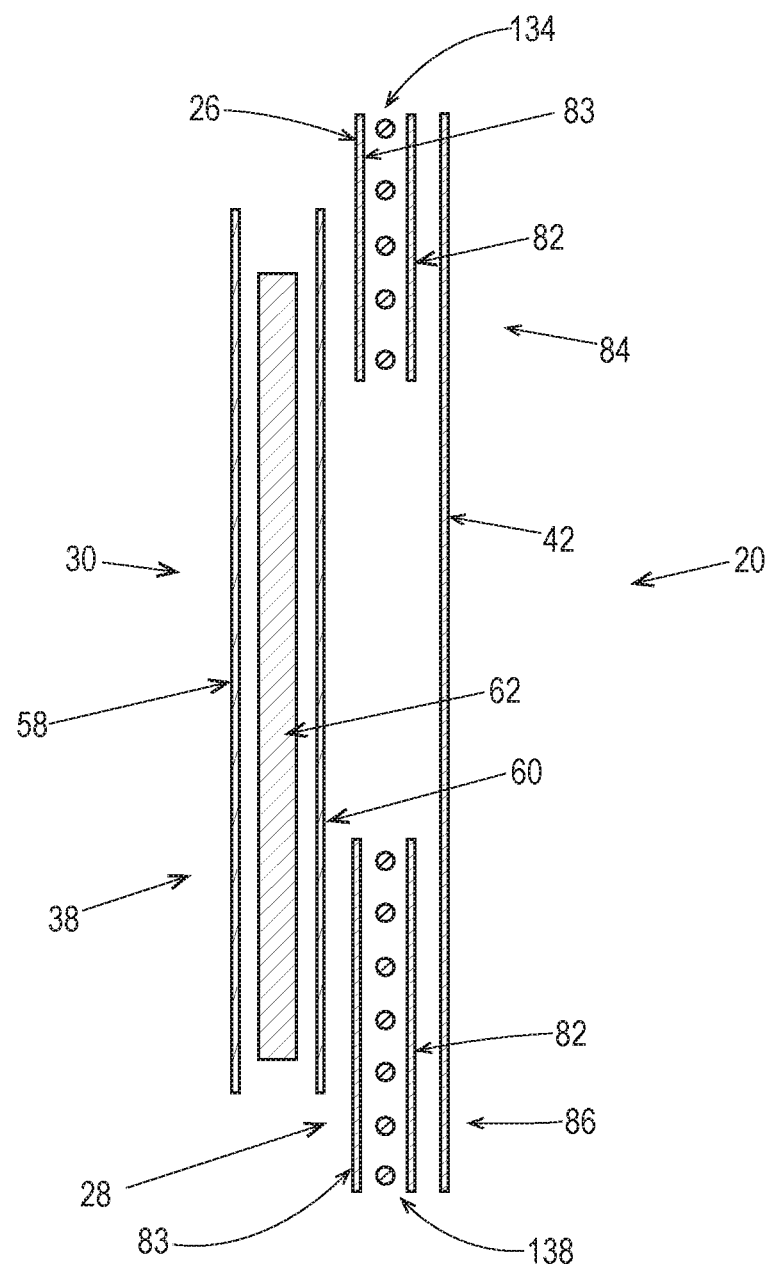
FIG. 4E is a schematic cross section view of a sixth embodiment taken along line 4-4 in FIG. 3 of an exemplary disposable pull-on garment.
Figure 4F:
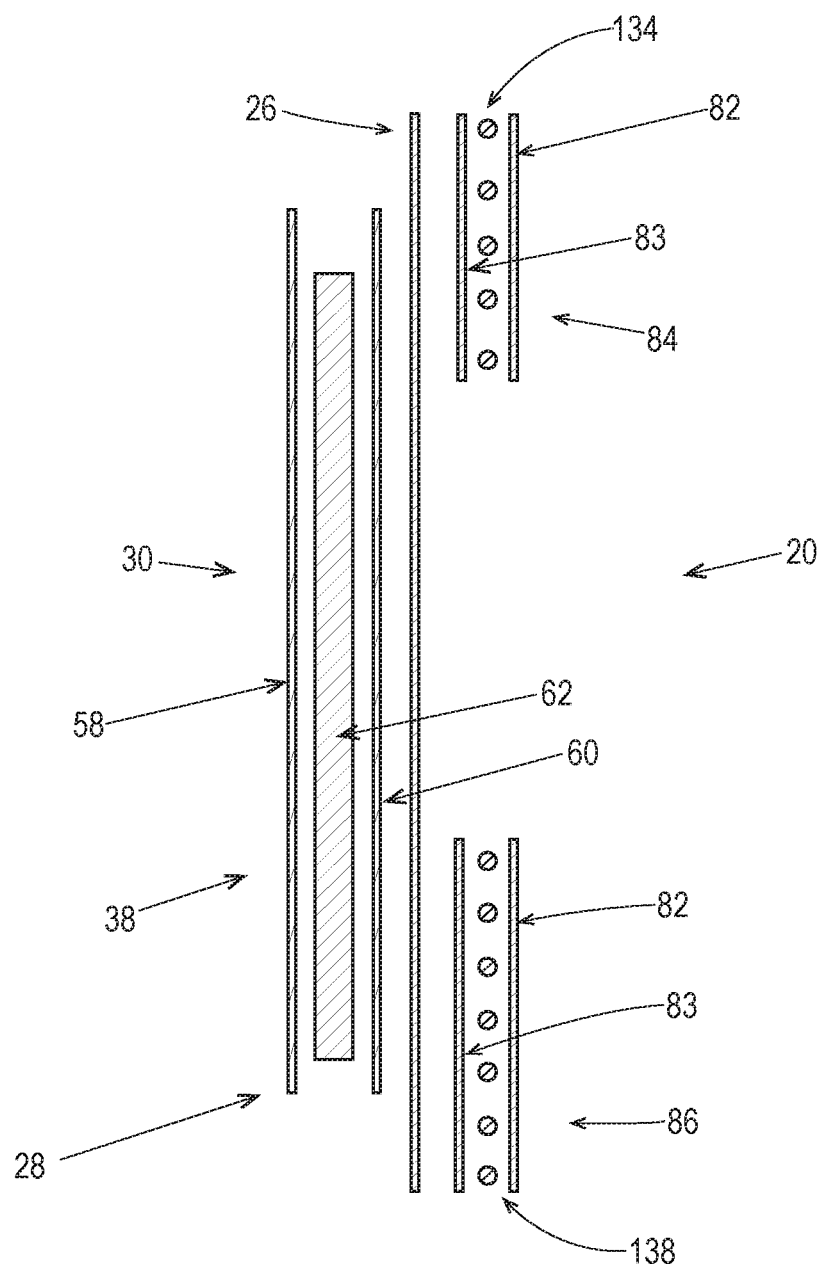
FIG. 4F is a schematic cross section view of a seventh embodiment taken along line 4-4 in FIG. 3 of an exemplary disposable pull-on garment.

In the embodiment shown in FIGS. 4E and 4F, the absorbent articles 20 may comprise a full outer cover layer 42, extending from a front waist edge 134 in a first waist region 26, through the crotch region to the longitudinally opposing rear waist edge 138 in a second waist region 28. The article may also comprise front and rear belts 84, 86 intended to encircle the waist of the wearer, the front and rear belts 84, 86 being connected to the outer cover layer 42 and/or the main body 38 of the absorbent article 20. The first and second belts are formed from a first belt layer forming a portion of the outer surface of the belt, the first belt layer being formed of two longitudinally spaced webs of material. The first and second belt portions also comprise a second belt layer forming a portion of the inner surface of the absorbent article, the second belt layer also being formed of two longitudinally spaced webs of material. The first and second belt layers may be formed of substantially the same material or may comprise different materials. The first and second belt layers may be formed from nonwovens, films, foams or combinations thereof. The first and second belts may also comprise an elastomeric material disposed between the first and second belt layers. The elastomeric material may comprise elastic strands, elastomeric films, elastomeric ribbons, elastomeric nonwovens, elastomeric filaments, elastomeric adhesives, elastomeric foams, scrims or combinations thereof. The first and second belts may be disposed on the interior surface of the outer cover layer. Alternatively, the first and second belts may be disposed on the outer surface of the outer cover layer. In such an embodiment the outer cover layer would for a portion of the inner surface of the article in the waist regions and the first belt layer would form a portion of the outer surface of the article. The second belt layer when present may be disposed between the first belt layer and the outer cover layer. The main body 38 of the absorbent article 20 may comprise an outer surface 22, backsheet 60, an inner surface 24, topsheet 58, and an absorbent core 62 disposed between the topsheet 58 and the backsheet 60. In addition, the main body 38 may comprise elasticized barrier leg cuffs 64 disposed at or adjacent the side edges of the main body 38. One or both of the front and rear belts 84, 86 may overlap at least a portion of the main body 38 and one or both of the belts may be disposed on the outer surface of the main body 38 or alternatively on the inner surface of the main body 38. One or both of the front and rear belts 84, 86 may be disposed on the interior surface of the outer cover layer or alternatively one or both of the belts may be disposed on the exterior surface of the outer cover layer. One or both of the front belt and rear belt 84, 86 may comprise longitudinally spaced webs of material forming a first surface of the belt wherein the webs are folded along the waist edge 36 of the belt to wrap the elastomeric material and form at least a portion of the second surface of the belt. In other words, a portion or the entirety of the inner surface and outer surface of one or both of the belt portions may be formed from a single web of material. The rugosities, wrinkles, folds in one or both of the front and rear belts may have a different configuration, size, orientation, shape, etc. than that of the outer cover layer.

Figure 4G:
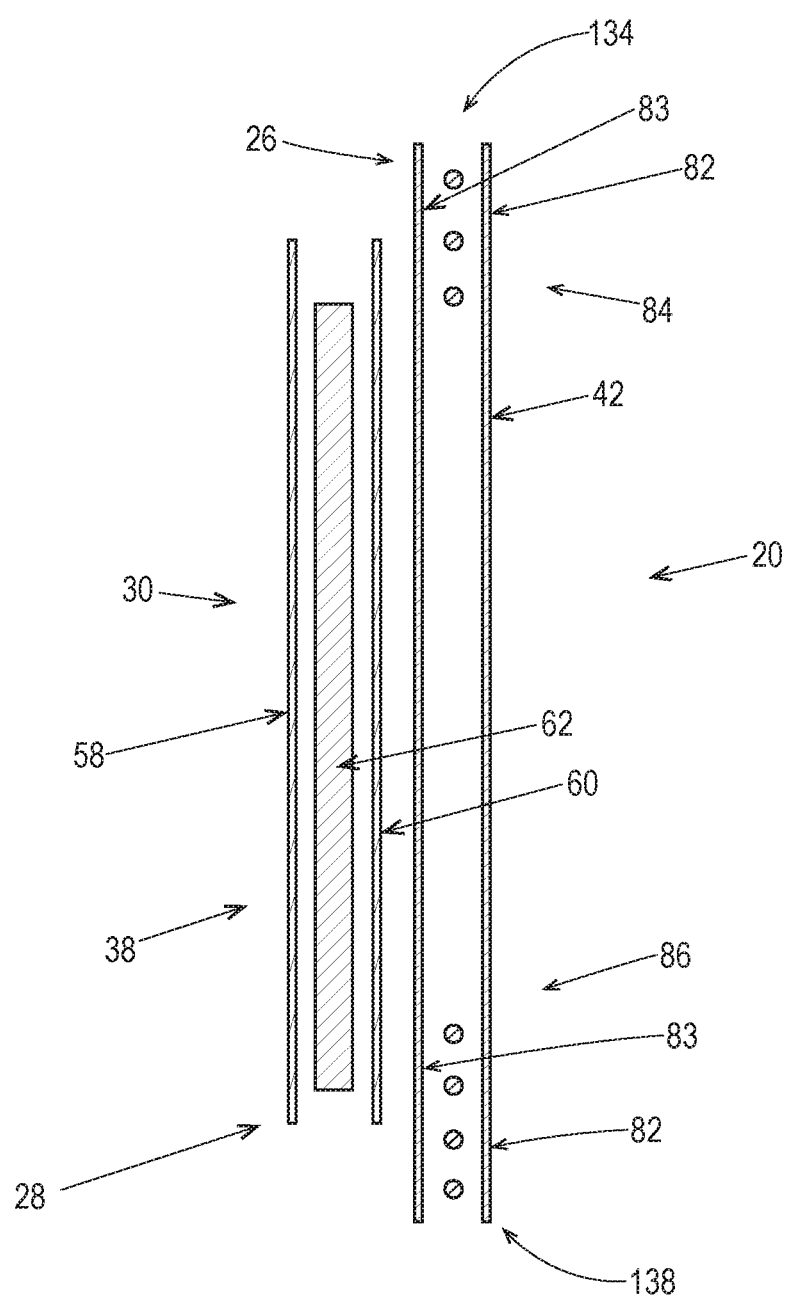
FIG. 4G is a schematic cross section view of an eight embodiment taken along line 4-4 in FIG. 3 of an exemplary disposable pull-on garment.

In the embodiment shown in FIG. 4G, the absorbent articles 20 may comprise front and rear belts 84, 86 intended to encircle at least a portion of the waist of the wearer, the front and rear belts 84, 86 being connected to a main body 38 forming a portion of the crotch region 30 of the absorbent article 20. The front and rear belts 84, 86 are formed from a first belt layer 82 forming a portion of the outer surface of the absorbent article. The front and rear belt portions 84, 86 also comprise a second belt layer 83 forming a portion of the inner surface 24 of the absorbent article 20. The second belt layer may be laterally discontinuous and spaced apart in a transverse direction. The first and second belt layers 82, 83 may be formed of substantially the same material or may comprise different materials. The first and second belt layers 82, 83 may be formed from nonwovens, films, foams or combinations thereof. The front and rear belt portions 84, 86 may also comprise an elastomeric material disposed between the first and second belt layers 82, 83. The elastomeric material may comprise elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer. The main body 38 of the absorbent article may comprise an outer surface 22, backsheet 60, an inner surface 24, topsheet 58, and an absorbent core 62 disposed between the topsheet 58 and the backsheet 60. In certain embodiments the backsheet may be a nonwoven and film laminate wherein the nonwoven is formed by the outer cover layer. In addition, the main body 38 may comprise elasticized barrier leg cuffs 64 disposed at or adjacent the side edges of the main body 38. The front and rear belts 84, 86 overlap at least a portion of the main body 38 and one or both of the belts may be disposed on the outer surface of the main body 38. A portion of the second belt layer and/or a portion of the first belt layer may be directly attached to the outer cover layer. The front and rear belts 84, 86 may be formed from a first belt layer extending from a first waist edge 134 in a first waist region 26 through the crotch region to a second waist edge 138 in a second waist region 28 and forming a portion of the outer surface of the absorbent article 20. The front and rear belts 84, 86 may also comprise a second belt layer extending from a first waist edge 134 in a first waist region 26 through the crotch region to a second waist edge 138 in a second waist region 28 and forming a portion of the inner surface of the absorbent article 20. The first and second belt layers may be formed of substantially the same material or may comprise different materials. The first and second belt layers may be formed from nonwovens, films, foams, woven materials or combinations thereof. The front and rear belt portions 84, 86 may also comprise an elastomeric material disposed between the first and second belt layers in one or both of the first and second waist regions 26, 28. The elastomeric material may comprise elastic strands, elastomeric films, elastomeric ribbons, elastomeric nonwovens, elastomeric filaments, elastomeric adhesives, elastomeric foams, scrims or combinations thereof. The main body 38 of the absorbent article 20 may comprise an outer surface 22, backsheet 60, an inner surface 24, topsheet 58, and an absorbent core 62 disposed between the topsheet 58 and the backsheet 60. One or both of the first and second belt layers may form a portion of the outer surface 22. In addition, the main body 38 may comprise elasticized barrier leg cuffs 64 disposed at or adjacent the side edges of the main body 38. A portion of one or both of the front and rear belts 84, 86 may overlap at least a portion of the main body 38. Alternatively, the front belt portion and rear belts 84, 86 may comprise a belt layer forming a first surface of the belt portion wherein the belt layer may be folded along the waist edge of the belt portion to wrap the elastomeric material and overlap a portion of the opposing belt layer. In other words, a portion of the inner surface and a portion of the outer surface of each of the belt portions may be formed from a single web of material.

A portion or the whole of the main body 38 may be made extensible to a degree greater than the inherent extensibility of the material or materials from which the main body 38 is made, e.g., the backsheet 60. The additional extensibility may be desirable in order to allow the main body 38 to conform to the body of a wearer during movement by the wearer and or to provide adequate body coverage. The additional extensibility may also be desirable, for example, in order to allow the user of a absorbent article including a main body 38 having a particular size before extension to extend the front waist region 26, the back waist region 28, or both waist regions of the main body 38 to provide additional body coverage for wearers of differing size, i.e., to tailor the article to the individual wearer. Such extension of the waist region or regions may give the main body 38 a generally hourglass shape, so long as the crotch region is extended to a relatively lesser degree than the waist region or regions, and may impart a tailored appearance to the article when it is worn. In addition, the additional extensibility may be desirable in order to minimize the cost of the article 10. For example, an amount of material that would otherwise be sufficient only to make a relatively smaller article lacking this extensibility can be used to make an article capable of being extended to adequately cover a wearer that is larger than the unextended smaller absorbent article would fit.

A portion of the main body 38, for example a portion of the chassis in one or both of the waist regions 26, 28 may be made laterally extensible to a maximum extensibility greater than a maximum extensibility of another portion of the main body 38 in the crotch region such that a lateral extension of each of the portions to its maximum extensibility imparts an hourglass shape to the main body 38. In one embodiment, the portion of the main body 38 underlying and/or immediately adjacent one or both of the front and back extensible belts may be made laterally extensible to a maximum extensibility greater than a maximum extensibility of another portion of the main body 38, for example the crotch region, such that a lateral extension of each of the portions to its maximum extensibility facilitates application of the absorbent article onto the body of a wearer by enabling the waist regions to be extended to fit over the wearer's hips and in addition, opening and orienting the leg openings enabling the wearer to place the legs through the openings more effectively.

Additional lateral extensibility in the main body 38 may be provided in a variety of ways. For example, a material or materials from which the main body 38 is made may be pleated by any of many known methods. Alternatively, all or a portion of the main body 38 may be made of a formed web material or a formed laminate of web materials like those described in U.S. Pat. No. 5,518,801 issued on 21 May 1996 in the name of Chappell et al. This formed web material includes distinct laterally extending regions in which the original material has been altered by embossing or another method of deformation to create a pattern of generally longitudinally oriented alternating ridges and valleys and also includes laterally extending unaltered regions between the laterally extending altered regions. The formed web material can be extended in a direction perpendicular to the ridges up to the point where the ridges and valleys flatten with substantially less force than is required to extend beyond that point. In addition to lateral extensibility, the creation of a formed laminate web as described above provides a main body 38 backsheet with improved texture and cloth-like appearance and feel. The deformation creates a cloth-like pattern in the film and increases the loft of the nonwoven in multi-layer film and nonwoven laminate backsheets.

Alternatively, a portion of the absorbent article can be ring-rolled and thus rendered highly extensible as described in U.S. Pat. No. 5,366,782 (issued Nov. 22, 1994 to Curro, et al). Specifically, a ring-rolling apparatus includes opposing rolls having intermeshing teeth that incrementally stretch and thereby plastically deform the material forming the absorbent article (or a portion thereof) thereby rendering the article extensible in the ring-rolled regions. In one embodiment, the absorbent article can be ring-rolled in a portion of at least one of the front or back waist regions, for example the portion of the main body 38 underlying and/or immediately adjacent one or both of the front and back belts 84, 86, while other regions may comprise a structured elastic-like formed web material. The article may be ring-rolled across the entire width in one or both of the waist regions or alternatively may be ring-rolled over only a portion of the main body 38 width or over only a portion of one or both of the belts.

The front laterally central portion and the back laterally central portion of the main body 38 may have a different range of extensibility from other portions of the main body 38. Additionally or alternatively, the laterally central portions may be extensible to a greater or lesser degree when subjected to a given level of opposing tensile forces, i.e., may be more easily or less easily extensible, than other portions of the main body 38.

Figure 5A:
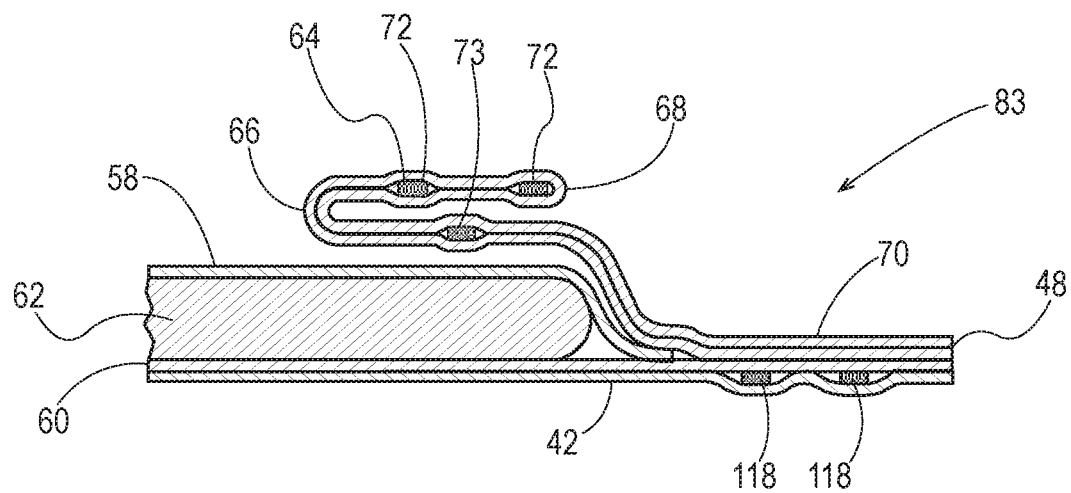
FIG. 5A is a schematic cross section view taken along line 5-5 in FIG. 3 of an example of a folded outer leg cuff suitable in one embodiment of the invention.

The main body 38 may comprise a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 5 comprises a single layer of material which may be folded to form a barrier leg cuff having two layers. The barrier leg cuff 64 extends from the side of the main body at or adjacent the longitudinal side edge 48 toward the longitudinal centerline L2. The barrier leg cuff may be folded along the folding line 66 back toward the longitudinal side edge 48. The barrier leg cuff 64 may have a first barrier cuff elastic material 72 adjacent to the distal portion 68 and a second barrier cuff elastic material 73 adjacent to the proximal portion 70 of the barrier leg cuff 64. The proximal portion 70 of the barrier leg cuff 64 may be joined to the backsheet 60 adjacent to the longitudinal side edge 48. The portion of the barrier leg cuff 64 along the folding line 66 and the distal portion 68 may be free from attachment to any portion of the main body 38 in the crotch region 30 such that the barrier leg cuff 64 stands up toward the wearer's body. The transverse end 74 of the barrier leg cuff 64 may be joined to the topsheet 58 at or adjacent the longitudinally opposing ends of the leg cuff by an attachment means which may be any known means such as an adhesive, heat bond, pressure bond or the like as shown in FIG. 5A. Examples of acceptable cuffs 64 are disclosed in U.S. Ser. No. 13/457, 521, filed Apr. 27, 2012, including the configurations disclosed by FIGS. 8a-t. For, instance, as illustrated in FIG. 5B, the barrier leg cuff may be a two-piece cuff And, the cuff 64 may be joined to the backsheet with a no leak bead 215 that runs along the entire longitudinal length of the cuff and/or the backsheet film 60.

The liquid pervious topsheet 58 may be positioned adjacent the body-facing surface of the absorbent core 62 and may be joined thereto and/or to the backsheet 60 by any attachment means known in the art. The liquid impervious backsheet 60 is generally that portion of the absorbent article 20 positioned adjacent the garment-facing surface of the absorbent core 62 and prevents the exudates absorbed and contained therein from soiling articles that may contact the absorbent article 20. The absorbent core is positioned between the topsheet 58 and the backsheet 60 and absorbs and retains liquids such as urine and other certain body exudates.

The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet.

A suitable absorbent core for use in the absorbent article 20 may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core may comprise a fluid acquisition component, a fluid distribution component, and a fluid storage component. An example of a suitable absorbent core having a fluid acquisition component, a fluid distribution component, and a fluid storage component is described in U.S. Pat. No. 6,590,136. Examples of acceptable air felt free cores (i.e., absorbent core systems having little or no air felt) are disclosed in U.S. Pat. Nos. 5,562,646, 7,750,203, 7,744,576 and U.S. Pub. Nos. 2008/0312617A1, 2008/0312619A1, and 2004/0097895A1.

The outer cover layer 42 may be disposed on the outer surface 22 of the absorbent article 20 and covers the crotch panel 56 of the absorbent main body 38. The outer cover layer 42 may extend into and cover the front waist panel 52 and the back waist panel 54 of the main body 38. The outer cover layer may form a portion of the backsheet and/or the main body. The outer cover layer 42 may be directly joined to and cover a portion or all of the liquid impervious backsheet 60 of the main body 38. The central panel 80 of the front and back belt 84, 86 may be joined to the front waist panel 52 and the back waist panel 54 of the main body 38 through the outer cover layer 42. Thus, the outer cover layer 42 is disposed between the front and back belt 84, 86 and the liquid impervious backsheet 60 of the main body 38. In one embodiment shown in FIGS. 2 and 4C, the outer cover layer 42 is coextensive with the liquid impervious backsheet 60. The leg elastic material 140 is disposed so as to extend generally longitudinally along the longitudinal side edge 48 of the main body 38. The leg elastic material 140 may be disposed at least in the crotch region 30 of the absorbent article 20 or may be disposed along the entirety of the longitudinal side edge 48.

The outer cover layer 42 may comprise a material separate from the material of the inner layer 83 and the outer layer 82 constituting the belt 40. The outer cover layer 42 may comprise two or more layers of materials. The outer cover layer 42 may comprise any known materials and may comprise materials used for the front and back belt 84, 86 as explained above. The outer cover layer 42 may comprise a single layer of nonwoven web of synthetic fibers. The outer cover layer 42 may comprise a single layer of hydrophobic, non-stretchable nonwoven material. The outer cover layer may comprise a film, a foam, a nonwoven, a woven material or the like and/or combinations thereof such as a laminate of a film and a nonwoven.

The belt 40 may comprise a front belt 84 and a back belt 86 (hereinafter may be referred to as "front and back belt 84, 86) and has a ring-like configuration by permanently or refastenably connecting the front belt 84 and the back belt 86 at the seams 32 or by permanently or refastenably connecting the front and/or back belt to the main body 38. Articles of the present disclosure may have refastenable elements, configurations, and methods of making as disclosed in U.S. Ser. No. 61/787,416, filed on Mar. 15, 2013, as well as U.S. Ser. No. 61/787,332, filed on Mar. 15, 2013.

The belt 40 may be ring-like and elastic. The ring-like elastic belt 40 extends transversely about the waist opening 36 of the absorbent article 20 and acts to dynamically create fitment forces and to distribute the forces dynamically generated during wear. Applicants have found that improved fit can be created by controlling the distance between, linear density, and the pre-strain of the elastomeric material in relation to each other and to the openings for the body. This may occur by choosing different materials throughout the belt 40 that exhibit desired properties. The different materials are combined at specific distances, linear densities, and prestrains to create a belt 40 that acts to dynamically create fitment forces. Particularly, the articles of this disclosure may have the characteristics of the articles of Examples 1-4 as disclosed in U.S. Ser. No. 13/764,990, filed Feb. 12, 2013. Articles of the present disclosure may also have the same stress, strain and spacing of its elastics as disclosed in U.S.

Ser. No. 13/764,990 and/or as disclosed in U.S. Ser. No. 61/598,012, filed Feb. 13, 2012. Articles of the present disclosure may also have the same elastic sections and force zones disclosed in U.S. Ser. No. 13/764,990.

The front belt 84 may comprise 5 to 50 elastic strands. The front belt 84 may comprise 10 to 20 elastic strands. The back belt 86 may comprise 5 to 50 elastic strands. The back belt 86 may comprise 10 to 20 elastic strands. The elastic strands are distributed amongst the different force zones. Elastic strands may be distributed evenly amongst the force zones. Elastic strands may also be distributed unevenly amongst the different force zones. Each force zone comprises at least one elastic strand.

The elastic strands may have a linear density between 200 to 2500. Linear density is the density of the elastic fibers in the elastic strand. The most commonly used unit for the linear density is the decitex, abbreviated dtex, which is the mass in grams per 10,000 meters. The linear density may be used to change the force profile. For example, one could reach a desired force profile by selecting the linear density of a single elastic strand, combining multiple elastic strands with a smaller linear density in close proximity to each other, and/or combining with other elastomeric materials.

The elastic strands may have an elastic pre-strain. The elastic pre-strain is the percent of length increase in an elastic strand or plurality of elastic strands at the point of combining the elastic(s) with the first and/or second belt layers. For example a strand with a free length of 15 centimeters (cm) may have a load applied such that the 15 cm elastic strand is now 18 cm long. This length increase of 3 cm is 20% of 15 cm (3/15), or a 20% strain. The elastic pre-strain may be used to change the force profile of a single elastic strand or a plurality of elastic strands. Force profiles may also be changed by changing the linear density in conjunction with the elastic pre-strain of one or more elastic strands.

The number of elastic strands in each zone may be changed according to the placement of the absorbent core. Applicants have found that the use of thinner absorbent cores may lead to a need in increased elastic force to compensate for the change in article thickness. The force profile must be adjusted depending on the location and thickness of the absorbent core. This particularly affects the second elastic section and third elastic section.

The elastic strands disposed in the belt may be aligned in a curved fashion so that the a tangent of the curve of the elastic strands may form an acute angle with the centerline or may form an arcuate shape. This may allow for targeting the force profile and/or coordinating print and elastication/rugosities/elastics in the stretch sections.

It may be desirable to use the hot air seaming processes, as well as the article forming processes disclosed in U.S. Pat. No. 6,248,195 and U.S. Ser. Nos. 12/795,021, 13/401,907, and 13/402,056 for seaming articles as disclosed herein. And, the articles disclosed herein may have graphics in accordance with U.S. Ser. Nos. 61/646,953 and 61/646,979, each filed on May 15, 2012.

Test Methods Section
Test Equipment/Environment

A suitable tensile tester such as an MTS Alliance with MTS Testworks version 4.0 or equivalent instrument is used. The tester is equipped with flat clamps that are capable of holding at least the entire transverse length of the side seam should be used. The instrument is calibrated according to the manufacturer's specification. Testing is performed at 23° C.±2° C. and 50%±2% relative humidity.

Sample Prep

The side seams of the product are broken to separate the front belt from the back belt. The respective force zones (as described in the Detailed Description of the Invention) are cut away from these belts. Each separated section of the front and back belt will be referred to as a "test sample" herein. All material layers, including the chassis components, should be kept with the test sample. All cut lines are straight, parallel to the transverse direction of the absorbent article. Each test sample needs to have at least one elastomeric material. The widths (a dimension in the longitudinal direction of the absorbent article) of the respective zones are measured.

The length of the test sample is determined. The length measures in the transverse direction of the absorbent article a distance from one end to the other end of a test sample in a fully stretched condition. The fully stretched condition is the condition where the test sample is stretched by the force of 0.1 N/mm multiplied by the width of the test sample. If one or both ends of a test sample are not parallel to the longitudinal direction, the shortest length within the test sample is considered as the length of the test sample.

An adjusted test sample length is defined such that the length of a test sample minus the combined length of any material in the upper and lower clamps. Thus, if a test sample is mounted in the clamp so that 10 mm at each end is held in the clamps, then the adjusted belt length is the measured belt length minus 20 mm.

The test samples are kept unstretched at least for 10 min before the test.

Test

For each test sample, the initial gauge length of the tensile tester is set to allow the test sample to be mounted in a relaxed state. The load cell is zeroed to offset the sample weight.

The test sample is stretched in the transverse direction of the absorbent article at a rate of 254 mm/min, and a load (N) is measured within 5 sec after the test sample reaches at 65% of the adjusted test sample length. The transverse force is calculated for each of the force zones according to an equation:

$$\text{A transverse force (N/mm) of a test sample} = \text{Measured value (N)}/\text{width of the force zone (mm)}$$

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a front region, a crotch region, and a back region, the absorbent article comprising:
   a first inner belt web and a first outer cover web;
   a second inner belt web and a second outer cover web;
   a first plurality of elastics disposed between the first inner belt web and the first outer cover web;
   a second plurality of elastics disposed between the second inner belt web and the second outer cover web;
   first and second laterally opposed side seams joining the first and second inner belt webs together, such that a waist opening and first and second leg openings are formed;
   each of the laterally opposed side seams comprising a waist end edge and a leg end edge;
   a first axis from the leg end edge of the first side seam to the leg end edge of the second side seam, along the first inner belt web, the first axis defining the transition between the front region and the crotch region;
   the area between the first axis and a transverse axis of the absorbent article defining a front crotch region;
   a second axis from the leg end edge of the first side seam to the leg end edge of the second side seam, along the second inner belt, the second axis defining the transition between the back region and the crotch region;
   the area between the second axis and a transverse axis of the absorbent article defining a back crotch region;
   wherein the first plurality of elastics are disposed in the front region and the front crotch region;
   wherein the second plurality of elastics are disposed in the back region and the back crotch region;
   wherein the first inner belt extends longitudinally from the front region into the front crotch region;
   wherein the second inner belt extends longitudinally from the back region into the back crotch region; and
   wherein the first and second plurality of elastics consist of linear segments parallel with a transverse axis of the article; and
   a third plurality of elastic elements sandwiched between nonwoven layers to form an inner barrier cuff, the third plurality of elastics transversely proximal to a fourth plurality of elastic elements disposed against a backsheet film to form an outer barrier cuff.

2. The absorbent article of claim 1, further comprising a center chassis, the center chassis comprising a topsheet, an absorbent core, and a backsheet film.

3. The absorbent article of claim 2, wherein at least some portions of the first and second inner belt webs are directly joined to the backsheet film.

4. The absorbent article of claim 3, wherein a portion of at least one of the first outer cover web and the second outer cover web is directly joined to the backsheet film.

5. The absorbent article of claim 2, wherein at least one elastic element of the first plurality of elastics runs transversely across the absorbent core.

6. The absorbent article of claim 2, wherein at least one elastic element of the second plurality of elastics runs transversely across the absorbent core.

7. The absorbent article of claim 2, wherein the outer barrier cuff is joined to the topsheet and the backsheet film.

8. The absorbent article of claim 7, wherein the inner barrier cuff is joined to the outer barrier cuff.

9. The absorbent article of claim 1, wherein at least some portions of the first inner belt web forming at least some portions of the first and second leg openings are concave.

10. The absorbent article of claim 1, wherein at least some portions of the second inner belt web forming at least some portions of the first and second leg openings are concave.

11. The absorbent article of claim 1, wherein the first and second laterally opposed side seams joining the first and second inner belt webs together are refastenable.

12. The absorbent article of claim 1, wherein the first plurality of elastics are parallel with the transverse axis.

13. The absorbent article of claim 1, wherein the second plurality of elastics are parallel with transverse axis.

14. The absorbent article of claim 1, further comprising a central chassis comprising an absorbent core, wherein a portion of at least one of the first outer cover web and the second outer cover web overlaps the waist end edges and is joined to an interior surface of the central chassis.

15. The absorbent article of claim 14, wherein the portion of at least one of the first outer cover web and the second outer cover web that overlaps the interior surface of the central chassis also overlaps an interior surface of the absorbent core.

16. The absorbent article of claim 1, wherein the third plurality of elastics run parallel with the longitudinal axis.

17. The absorbent article of claim 16, wherein the fourth plurality of elastics run parallel with the longitudinal axis.

18. The absorbent article of claim 17, wherein the first and second plurality of elastics are interrupted such that they are do not overlap at least a portion the central chassis in the front and back regions.

19. The absorbent article of claim 18, wherein the second plurality of elastics are interrupted such that they are do not overlap at least a portion of the central chassis in the front and back crotch regions.

20. The absorbent article of claim 16, wherein a central portion of the barrier leg cuffs extend transversely outboard of at least one of the first outer cover web and the second outer cover web.

* * * * *